US011376350B2

(12) United States Patent
Gaspredes et al.

(10) Patent No.: US 11,376,350 B2
(45) Date of Patent: Jul. 5, 2022

(54) METHODS AND SYSTEMS OF FLUID MANAGEMENT IN SURGICAL PROCEDURES

(71) Applicant: Smith & Nephew, Inc., Memphis, TN (US)

(72) Inventors: Jonathan L. Gaspredes, Austin, TX (US); Jean Woloszko, Austin, TX (US); Rajitha Aluru, Austin, TX (US); David J. Miller, Austin, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 798 days.

(21) Appl. No.: 16/166,754

(22) Filed: Oct. 22, 2018

(65) Prior Publication Data

US 2019/0143010 A1 May 16, 2019

Related U.S. Application Data

(60) Provisional application No. 62/587,179, filed on Nov. 16, 2017.

(51) Int. Cl.
*A61M 1/00* (2006.01)
*A61B 1/015* (2006.01)
(Continued)

(52) U.S. Cl.
CPC .......... *A61M 1/0058* (2013.01); *A61B 1/015* (2013.01); *A61B 17/320016* (2013.01); *A61M 1/74* (2021.05); *A61M 3/022* (2014.02); *A61M 3/0216* (2014.02); *F04B 49/065* (2013.01);
*F04B 49/08* (2013.01); *F04B 49/20* (2013.01); *A61B 2217/005* (2013.01);
(Continued)

(58) Field of Classification Search
CPC .................. A61M 1/0058; A61M 1/74; A61B 17/320016
See application file for complete search history.

(56) References Cited

U.S. PATENT DOCUMENTS 5,380,280 A 1/1995 Peterson
5,586,973 A 12/1996 Lemaire et al.
(Continued)

FOREIGN PATENT DOCUMENTS

WO 15175484 A1 11/2015

*Primary Examiner* — Nathan R Price
*Assistant Examiner* — Courtney B Fredrickson
(74) *Attorney, Agent, or Firm* — Dickinson Wright PLLC; Mark E. Scott

(57) ABSTRACT

Fluid management in surgical procedures. At least some of the example embodiments are methods including: pumping surgical fluid through a tube to a surgical site by a fluid controller operating in a first mode, the first mode comprising a first relationship of fluid flow and pressure drop across the tube and cannula, and the first mode comprising a first set of proportional, integral, and differential (PID) parameters; and then pumping surgical fluid through the tube to the surgical site with the fluid controller operating in a second mode, the second mode comprising a second relationship of fluid flow and pressure drop across the tube and cannula, the second relationship different than the first relationship, and the second mode comprising a second set of PID parameters used, the second set of PID parameters different than the first set of PID parameters.

20 Claims, 7 Drawing Sheets

(51) Int. Cl.
*A61M 3/02* (2006.01)
*F04B 49/20* (2006.01)
*F04B 49/08* (2006.01)
*A61B 17/32* (2006.01)
*F04B 49/06* (2006.01)

(52) U.S. Cl.
CPC .............. *A61M 2205/3334* (2013.01); *A61M 2205/3344* (2013.01); *A61M 2205/3365* (2013.01); *A61M 2205/52* (2013.01); *F04B 2203/0409* (2013.01); *F04B 2205/04* (2013.01); *F04B 2205/09* (2013.01)

(56) References Cited

U.S. PATENT DOCUMENTS

| | | | |
|---|---|---|---|
| 5,800,383 | A | 9/1998 | Chandler et al. |
| 2003/0152482 | A1* | 8/2003 | O'Mahony ......... A61M 1/3656 422/44 |
| 2004/0133149 | A1 | 7/2004 | Haischmann et al. |
| 2007/0078370 | A1 | 4/2007 | Shener et al. |
| 2007/0249993 | A1 | 10/2007 | Mollstam et al. |
| 2008/0154185 | A1 | 6/2008 | Blight |
| 2010/0049119 | A1 | 2/2010 | Norman et al. |
| 2010/0076372 | A1 | 3/2010 | Hacker et al. |
| 2010/0228222 | A1 | 9/2010 | Williams et al. |
| 2013/0267779 | A1 | 10/2013 | Woolford et al. |
| 2015/0174314 | A1* | 6/2015 | Shener ................ A61M 3/0216 604/151 |
| 2016/0346454 | A1* | 12/2016 | Woolford ............ A61M 3/0216 |
| 2017/0106199 | A1 | 4/2017 | Woolford et al. |

\* cited by examiner

METHODS AND SYSTEMS OF FLUID MANAGEMENT IN SURGICAL PROCEDURES

CROSS-REFERENCE TO RELATED APPLICATIONS

This application claims the benefit of U.S. Provisional Application Ser. No. 62/587,179 filed Nov. 16, 2017 titled "Methods and Systems of Fluid Management in Surgical Procedures." The provisional application is incorporated by reference herein as if reproduced in full below.

BACKGROUND

Arthroscopic surgical procedures are procedures performed on a joint, such as a knee or shoulder, of a patient. In order to provide space within the joint to perform the procedure, the joint may be distended using a surgical fluid (e.g., saline solution). However, resection procedures within a joint sometimes result in minor bleeding and create tissue fragments, which can cloud visibility within the joint. To maintain visibility, a continuous fluid flow through the joint may be employed. However, maintaining the pressure to distend the joint while simultaneously maintaining flow through the joint presents challenges.

BRIEF DESCRIPTION OF THE DRAWINGS

For a detailed description of example embodiments, reference will now be made to the accompanying drawings in which.

DEFINITIONS

Figure 1:
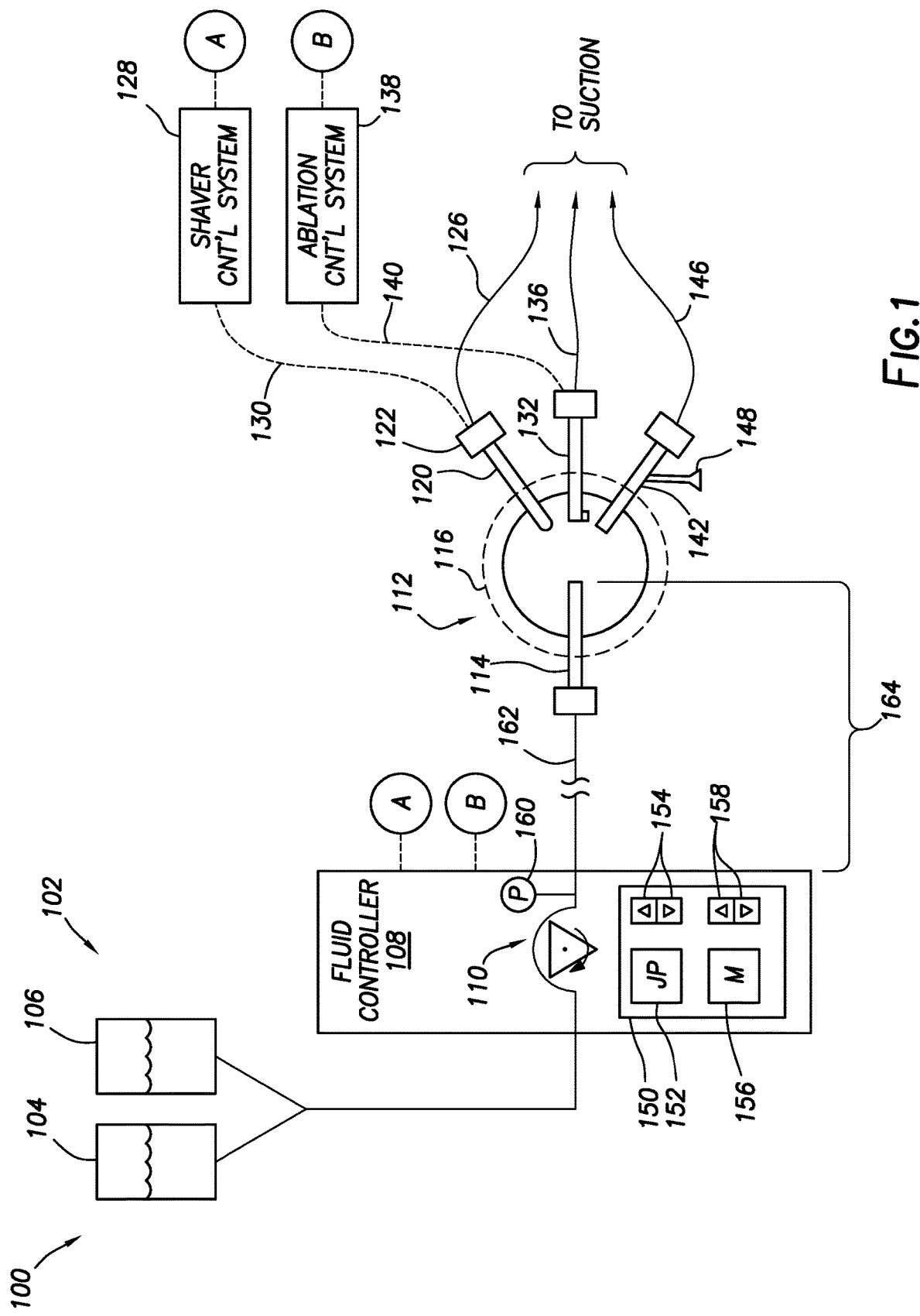
FIG. 1 shows a surgical system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Proportional, integral, and differential (PID) parameters" shall mean values associated with physical devices that implement a control loop, or values stored in software utilized by instructions that implement the control loop. However, the absence of a component of the control loop (e.g., the absence of a differential component) or values for a component that effectively remove the component (e.g., a zero multiplier for the differential component) shall not obviate the status of the values as PID parameters.

"Control system" shall comprise a field programmable gate array (FPGA), application specific integrated circuit (ASIC), programmable logic device (PLD), programmable logic controller (PLC), microcontroller, specifically implemented processor-based system, or combinations thereof configured to read electrical signals and take control actions responsive to such signals.

The terms "input" and "output" refer to connections (e.g., electrical, software), and shall not be read as verbs requiring action. For example, a control loop may have a set point input, a feedback input, and a speed control output. In systems implemented directly in hardware, these "inputs" and "outputs" define electrical connections. In systems implemented in software these "inputs" and "outputs" define parameters read by or written by, respectively, the instructions implementing the control loop.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to fluid management during surgical procedures, such as arthroscopic procedures. More particularly, example embodiments are directed to surgical systems that comprise a fluid controller. The fluid controller couples to a surgical site by way of a tube and in some cases a cannula. The fluid controller comprises a positive displacement pump and a control loop that controls speed of the positive displacement pump based on pressure of fluid within the surgical site. In many cases, the joint pressure within the surgical site is not directly measured, and thus the fluid controller infers joint pressure based on pressure of the surgical fluid measured at the outlet of the pump (e.g., positive displacement pump) and the flow of surgical fluid through the tube and cannula. The example fluid controller implements at least two modes of operation. The first mode utilizes a first relationship of fluid flow through the tube and pressure drop across the tube, and the first mode utilizes a first set of proportional, integral, and differential (PID) parameters used by a PID controller implemented by the fluid controller. The second mode comprises a second relationship of fluid flow through the tube and pressure drop across the tube, and the second mode utilizes a second set of PID parameters used by the PID controller. The second relationship is different than the first relationship, and the second set of PID parameters is different than the first set of PID parameters. The specification first turns to a brief description of why having a fluid controller with multiple modes may provide a competitive advantage in the marketplace.

Related-art fluid control systems are available from a variety of manufacturers. In most cases, the related-art fluid control systems do not directly measure or are not provided a direct measurement of fluid pressure within the joint during surgical procedures. Related-art fluid control systems attempt to address the issue using one of three methods. First, related-art fluid control systems utilize tubing sets and inflow cannulas that are of known flow resistance. Based on empirical testing, the relationship of fluid flow through the tubing sets and cannulas and pressure drop across the tubing sets and cannulas is known. By informing the related-art fluid control systems of the identity of the tubing set and cannulas, the related-art fluid control systems can calculate pressure within the surgical site based on pressure created by the pump and the known fluid flow characteristic through the tubing set. However, there is no requirement that a surgeon use a pre-characterized cannula with the fluid control systems, and thus there are circumstances in which the relationship of the fluid flow through the cannula and pressure drop across a cannula is not known by the fluid control systems. There is a third method in which the fluid control system does not try to compensate for the pressure drop across the tubing set.

In other cases in the related art, the relationship of the fluid flow through the tubing set and cannula and pressure drop across the tubing set and cannula is determined based on a calibration procedure performed just prior to the surgical procedure, with the tubing set and cannula to be used in the surgical procedure. The calibration procedure is time consuming, and for a surgical team that does not perform the calibration procedure regularly, the task can be daunting given that mis-calibration can result in over pressure and thus extravasation. Moreover, given the many tubes and devices in the surgical fluid flow path to the surgical site, the calibration is easily mishandled. For example, some surgical implements (e.g., inflow cannula) have fluid flow control valves the surgeon may modulate during surgery. If one of the valves is incorrectly positioned during the calibration procedure (e.g., closed when supposed to be open, or partially closed when supposed to be open), the results of the calibration may be incorrect and yet the surgery may continue with the unrealized associated risks.

Notwithstanding knowing or calibrating to determine the relationship of the fluid flow through the tubing set and pressure drop across the tubing set, personal preference of surgeons differs regarding how a fluid control system should operate during a surgical procedure. For purposes of explanation surgeons are conceptually divided in two opposing groups: a conservative group; and an aggressive group. It will be understood that the groups are presented for purposes of explanation, and in reality the two opposing groups define opposite ends of a spectrum. With respect to the conservative group, these surgeons may avoid pressure at which extravasation may occur. It is noted that extravasation pressure is not precisely know, and thus surgeons may estimate the extravasation pressure based on their clinical experience and experience with a particular pump. With lower pressure comes reduced surgical fluid flow (e.g., saline flow) and higher potential for bleeding. Reduced flow of surgical fluid may result in reduced visibility, as flushing of blood and tissue fragments may be slower. Surgeons in the conservative group may prefer fluid control systems that do not maintain the joint pressure at the set point pressure as pressure drops across the tubing set and inflow cannulas (i.e., un-compensated pumps/systems). Surgeons in the conservative group also may prefer that the pump be relatively slow to react to pressure changes in the joint (whether directly measured or inferred). Relatedly, many procedures are fixed-fee procedures, and by keeping joint pressure low (and thus fluid flow low) the total amount of surgical fluid used during the procedure is reduced, thus reducing fixed costs. With respect to the aggressive group, these surgeons may tolerate operating at higher joint pressures to achieve increased visibility throughout the surgical procedure. While higher pressure comes with increased surgical fluid flow to the joint, the increased surgical fluid usage may be offset to some extent by reduced surgical times. Surgeons in the aggressive group may prefer fluid control systems that maintain the joint pressure at the set point pressure by compensating for pressure drop across the tubing set and quickly reacting to pressure changes in the joint (whether directly measured or inferred). Related-art fluid control systems do not have the ability to "change their stripes" (e.g., between a very conservative system and a very aggressive system, or anywhere between). Thus, a surgical hospital or outpatient facility may be required to purchase and maintain multiple fluid control systems to satisfy the varying preferences of surgeons.

Various embodiments are directed to methods and related systems of fluid management in surgical procedures. More particularly, various embodiments are directed to a fluid controller for surgical procedures that selectively operates in various modes. For example, the surgeon may select an aggressive or performance mode where the fluid controller maintains the joint pressure via compensation and quickly reacts to pressure changes in the joint, thus providing increased visibility taking into account increased pressure in the joint and possibly increased use of surgical fluid during the surgical procedures. The surgeon may also select a conservative or economy mode where the fluid controller is not compensated such that pressure in the joint drops as flowrate increases, and the fluid controller is slow to react to pressure changes in the joint, potentially resulting in decreased visibility but lowering overall the pressure within the joint and decreasing use of surgical fluid during the surgical procedures. While two example modes are given here corresponding to the opposite ends of the spectrum noted above, any number of modes may be implemented. The technical solution to implement the varying modes is each mode uses a distinct relationship of fluid flow to the surgical site and pressure drops across the tube and cannula, and each mode may use a different set of control loop parameters to control how quickly the fluid controller responds to pressure excursions in the joint. These relationships and parameter implement the various modes. The specification now turns to an example system.

FIG. 1 shows a surgical system 100 in accordance with at least some embodiments. In particular, FIG. 1 shows a source of surgical fluid 102 in the form of saline bags 104 and 106. The example source of surgical fluid 102 fluidly couples to a fluid controller 108 comprising a positive displacement pump 110, the positive displacement pump illustratively shown as a peristaltic pump (and hereafter just peristaltic pump 110). The suction inlet of the peristaltic pump 110 is coupled to saline bags 104 and 106, and its discharge is fluidly coupled to the surgical site 112. In example systems, the surgical fluid is provided to the surgical site 112 by an instrument in the form of inflow cannula 114 having an internal channel fluidly coupled to the surgical site 112. The pressure of fluid within the surgical site may distend the surgical site slightly, such as shown by the dashed line 116 around the surgical site 112. The amount of distention will vary with pressure as well as the rigidity of the tissue surrounding the surgical site. The surgical site may be, for example, a knee, a shoulder, a hip, an ankle, or a wrist of the patient.

The example surgical system 100 further comprises a plurality of instruments associated with the surgical site out which fluid may flow; however, various embodiments are applicable to any situation in which surgical fluid flows from the surgical site 112, including surgical fluid flowing directly out an incision through the skin of the patient. The example surgical system 100 comprises a first instrument in the form of a mechanical resection device 120, such as a blade, burr device, or "shaver." So as not to unduly complicate the disclosure, the mechanical resection device 120 will be referred to as shaver 120 with the understanding that any mechanical resection device may be used. The shaver 120 may comprise a tubular member that defines an internal channel in communication with a distal opening, and a mechanical blade in operational relationship to the distal opening. The mechanical blade may be turned or oscillated by a motor (e.g., a motor within handle 122). The shaver 120 may be fluidly coupled to a source of suction (e.g., wall suction in a surgical room, a peristaltic pump, or other vacuum pump) by way of tube 126, and may be electrically coupled to a shaver control system 128 by way of an electrical connection 130 (electrical connection shown in dashed lines in FIG. 1 to avoid confusion with tubular connections). In operation, the shaver control system 128 provides electrical energy to the motor in the handle 122, which motor oscillates or turns the mechanical blade at the distal tip. The mechanical blade and distal opening may be placed proximate to tissue to be removed or resected, and the mechanical blade motion may cut the tissue and thereby create tissue fragments. Moreover, the tissue fragments and fluid within the joint may be drawn through the channel inside the shaver 120 by tube 126. In some example systems, the shaver control system 128 may be electrically coupled (shown by bubble "A") to the fluid controller 108 such that the fluid controller 108 can proactively respond to activation of the shaver 120 (discussed more below).

Another example instrument that may be used is an ablation device. In particular, the example surgical system 100 further comprises an ablation device 132. The ablation device 132 may comprise a tubular member that defines an internal channel in communication with a distal opening, and a metallic electrode in operational relationship to the distal opening and disposed within the surgical site 112. The ablation device 132 may be fluidly coupled to a source of suction (e.g., wall suction in a surgical room, or a peristaltic pump) by way of tube 136, and may be electrically coupled to an ablation control system 138 by way of an electrical connection 140 (shown with a dashed line). In operation, the ablation control system 138 provides electrical energy to the metallic electrode, which creates plasma near the metallic electrode. The metallic electrode and distal opening may be placed proximate to tissue to be removed or resected, and the plasma may volumetrically reduce and/or disassociate the tissue, creating tissue fragments and ablation by-products. Moreover, the tissue fragments, ablation by-products, and surgical fluid within the surgical site may be drawn through the channel inside the ablation device 132 by way of tubing 136. In some example systems, the ablation control system 138 may be electrically coupled (shown by bubble "B") to the fluid controller 108 such that the fluid controller 108 can proactively respond to activation of the ablation device 132 (discussed more below).

Before proceeding, it is noted that while theoretically possible to have both a shaver 120 and ablation device 132 inserted into the surgical site 112 at the same time, in many cases only one such instrument will be used, or will be used at any given time, and thus it is possible that a single entry point through the patient's skin into the surgical site 112 may be created and used for both the example classes of instruments. The instrument the surgeon chooses to use may be inserted into the entry point, used within the surgical site 112, and then withdrawn such that the second instrument can be inserted and used.

Still referring to FIG. 1, another example instrument that may be used is an outflow cannula 142. The outflow cannula 142 may comprise a tubular member that defines an internal channel in communication with a distal opening, and disposed within the surgical site 112. The outflow cannula may fluidly couple to a source of suction (e.g., wall suction in a surgical room, or a peristaltic pump) by way of tube 146. Thus, the outflow cannula 142 may be used to ensure fluid flow through surgical site 112. Although there are many alternatives to the surgical system 100 of FIG. 1, in some cases the outflow cannula 142 may also comprise optics for visualizing the inside of the surgical site, the optics illustrated by eyepiece 148 associated with the outflow cannula 142. In other example systems, the optics may be associated with the inflow cannula 114, and the outflow cannula 142 may be omitted or, if used, not have optics for visualization. In yet still other cases, inflow and outflow may be through a single cannula (with the inflow and outflow channels separated).

Still referring to FIG. 1, and returning to the fluid controller 108, the example fluid controller 108 further comprises a user interface 150 visible on or through an exterior surface of the fluid controller 108. The user interface 150 may take any suitable form, such as a display device (e.g., liquid crystal display (LCD)) with touch screen capabilities, or individually implement buttons and devices to display values. In the example system, the user interface 150 is designed and constructed to accept a setpoint joint pressure, as shown by setpoint joint pressure window 152 and buttons 154. Thus, by interfacing with the buttons 154 the surgeon may select a setpoint joint pressure as shown in the setpoint joint pressure window 152. Further in example embodiments, the user interface 150 is designed and constructed to accept an indication of a mode of operation of the fluid controller, as shown by mode window 156 and buttons 158. Thus, by interfacing with the buttons 158 the surgeon may select a mode (e.g., aggressive mode, conservative mode) as shown in the mode window 156.

In many cases the surgical system 100 will not directly measure pressure in the joint or surgical site 112. Rather, the fluid controller 108 could calculate or infer a joint pressure based on a pressure of surgical fluid measured at the outlet of the peristaltic pump 110 (as measured by pressure sensor 160) and pressure drop across the tube 162 and inflow cannula 114. That is, in some cases the length 164 of the tube 162 and inflow cannula 114 from the outlet of the peristaltic pump 110 to the surgical site 112 may be on the order of three to ten feet. Given the resistance to fluid flow through tube 162 and/or inflow cannula 114, a non-trivial pressure drop may occur across the length 164 in relation to setpoint joint pressure. Thus, by measuring the pressure at the outlet of the peristaltic pump 110, and knowing the flow through the tube 162 and inflow cannula 114, the joint pressure may be calculated as follows:

$$JP = MP - \Delta P \tag{1}$$

Where JP is the actual joint pressure, MP is the measured pressure at the outlet of the peristaltic pump 110, and ΔP is the pressure drop across the tube 162 and inflow cannula 114 as function of flow through the tube and inflow cannula.

Figure 2:
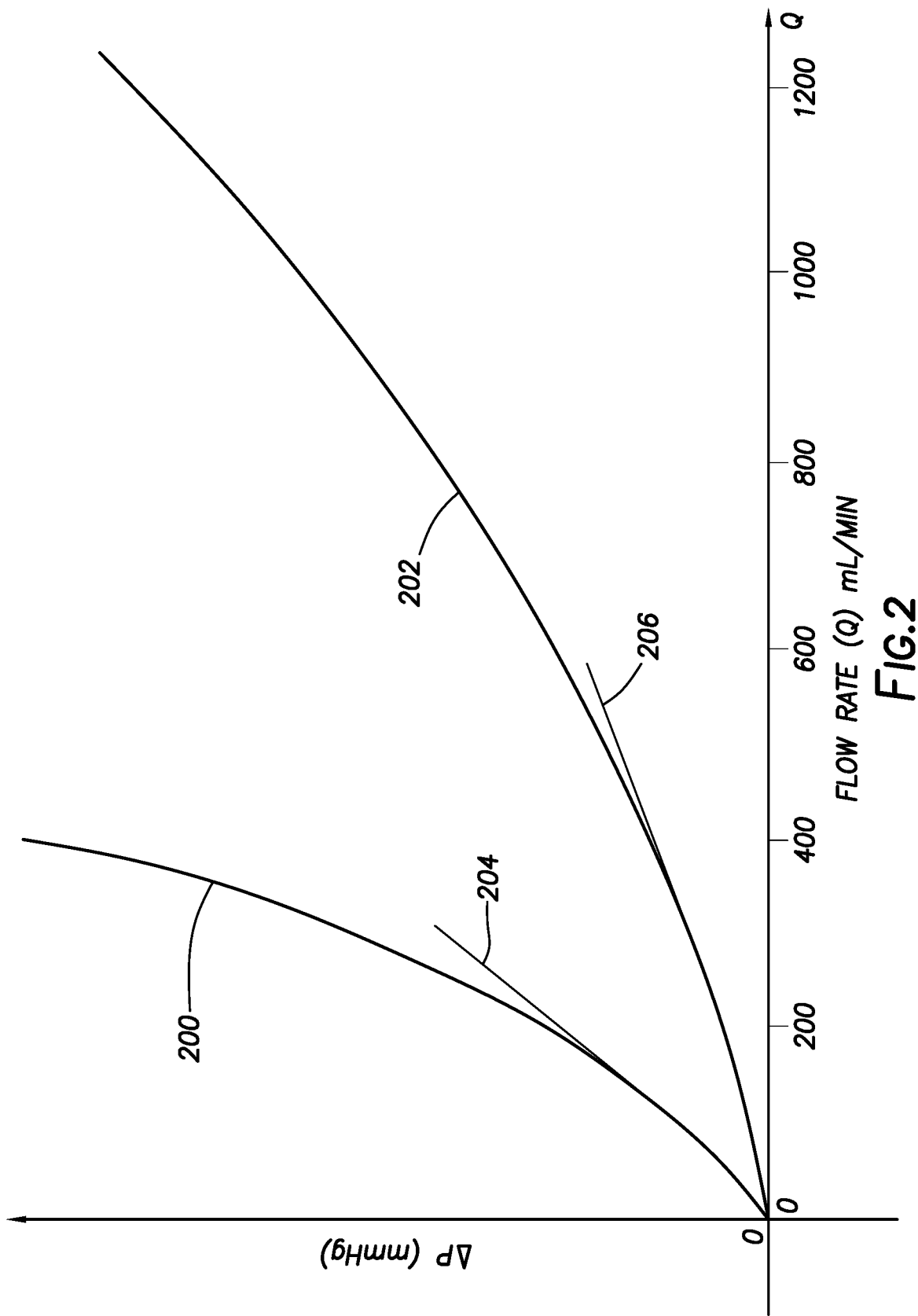
FIG. 2 shows a plot of pressure drop across the tubing and inflow cannula for two different tubing and cannula sets, in accordance with at least some embodiments.

FIG. 2 shows a plot of pressure drop across a tube and inflow cannula for two different assumed tube and inflow cannula sets, in accordance with at least some embodiments. In particular, the X axis (horizontal axis) is flow rate Q in milli-Liters per minute (mL/min), and the Y axis (vertical axis) is pressure drop (ΔP) across the tube and inflow cannula in millimeters of Mercury (mmHg). The plot of FIG. 2 shows two curves, comprising a first curve 200 and a second curve 202. Thus, the first curve 200 illustrates a first relationship between fluid flow through the tube and inflow cannula to pressure drop across the tube and inflow cannula. Likewise, the second curve 202 illustrates a second relationship of fluid flow through the tube and inflow cannula to pressure drop across the tube and inflow cannula, the second relationship different than the first relationship. More particularly still, first curve 200 shows a relationship where pressure drop increases at a first rate 204 (illustrated by a tangent line to the curve). The first curve 202 thus assumes higher resistance to surgical fluid flow (either in the tube, the inflow cannula, or both). Second curve 202 shows a relationship where pressure drop increases at a second rate 206 (illustrated by a tangent line to the curve) that is lower than the first rate 204. The second curve 202 thus assumes lower resistance to surgical fluid flow (either in the tubing, the inflow cannula, or both). Stated slightly differently, at a corresponding change in flow rate (e.g., between 200 mL/min and 210 mL/min) the first curve 200 pressure drop increases with fluid flow at a first rate 204, and in the second curve 202 pressure drop increases with fluid flow at a second rate 206, lower than the first rate 204.

In accordance with example systems, each mode of the fluid controller 108 uses a different relationship of fluid flow to pressure drop. Providing surgical fluid to the surgical site 112 based on a setpoint joint pressure and without measuring the actual joint pressure, in a first mode the fluid controller 108 may infer joint pressure based on the first curve 200 and using Equation (1) above. That is, by measuring outlet pressure at the outlet of the peristaltic pump 110 (such as measuring by way of pressure sensor 160), and determining a value proportional to flow rate of the surgical fluid to the surgical site 112, the fluid controller 108 may use the first curve 200 to determine a presumed pressure drop (ΔP) across the tube and inflow cannula. The fluid controller 108 may then adjust a control parameter based on the presumed pressure drop. In a second mode the fluid controller 108 may infer joint pressure based on the second curve 202 and using Equation (1) above. That is, by measuring outlet pressure at the outlet of the peristaltic pump 110 (such as measuring by way of pressure sensor 160), and determining a value proportional to flow rate of the surgical fluid to the surgical site 112, the fluid controller 108 may use the second curve 202 to determine a presumed pressure drop across the tubing and inflow cannula. The fluid controller 108 may then adjust a control parameter based on the presumed pressure drop. For a positive displacement pump such as peristaltic pump 110, the speed of the pump is directly related to the flow through the pump. It follows that, in either example mode, speed of the pump may be the value proportional to flow rate, or the speed of the pump may be translated to a value proportional to flow rate for use with the example relationships shown in FIG. 2.

A few points before proceeding. First, in accordance with example embodiments, the curves 200 and 202 are assumed relationships between flow rate and pressure drop that may not accurately reflect actual pressure drop across the tube 162 and inflow cannula 114. That is, in some cases the identity of the tubing set (that includes tube 162) and inflow cannula are not provided to the fluid controller 108, and no calibration is performed to establish the actual pressure versus flow curves. However, for reasons discussed in greater detail below, performing calibration or expressly identifying the tube and inflow cannula are not needed. While FIG. 2 shows two curves 200 and 202, two or more curves corresponding two or more modes may be used. Further still, while the example curves 200 and 202 are shown as lines having actual curvature, straight line relationships may also be used, each straight line relationship having a different slope. FIG. 2 shows the relationship as pressure drop as a function of flow rate; however, any value proportional to flow rate (e.g., peristaltic pump speed) may be used in the curves. Finally, while FIG. 2 shows the relationships as plots, the relationships may be implemented in any suitable form. For example, each relationship may be reduced to a mathematical formula, and calculating the pressure drop as a function of flow rate may involve applying the flow rate (or value indicative of flow rate) to the equation to calculate the pressure drop, and then applying Equation (1) above to infer joint pressure. As another example, each relationship may be implemented in the form of a lookup table, and determining the pressure drop as a function of flow rate may involve a lookup function based on the flow rate (or value indicative of flow rate) within the lookup table to determine the pressure drop. The specification now turns to a description of the control loops implemented in accordance with example embodiments.

Figure 3:
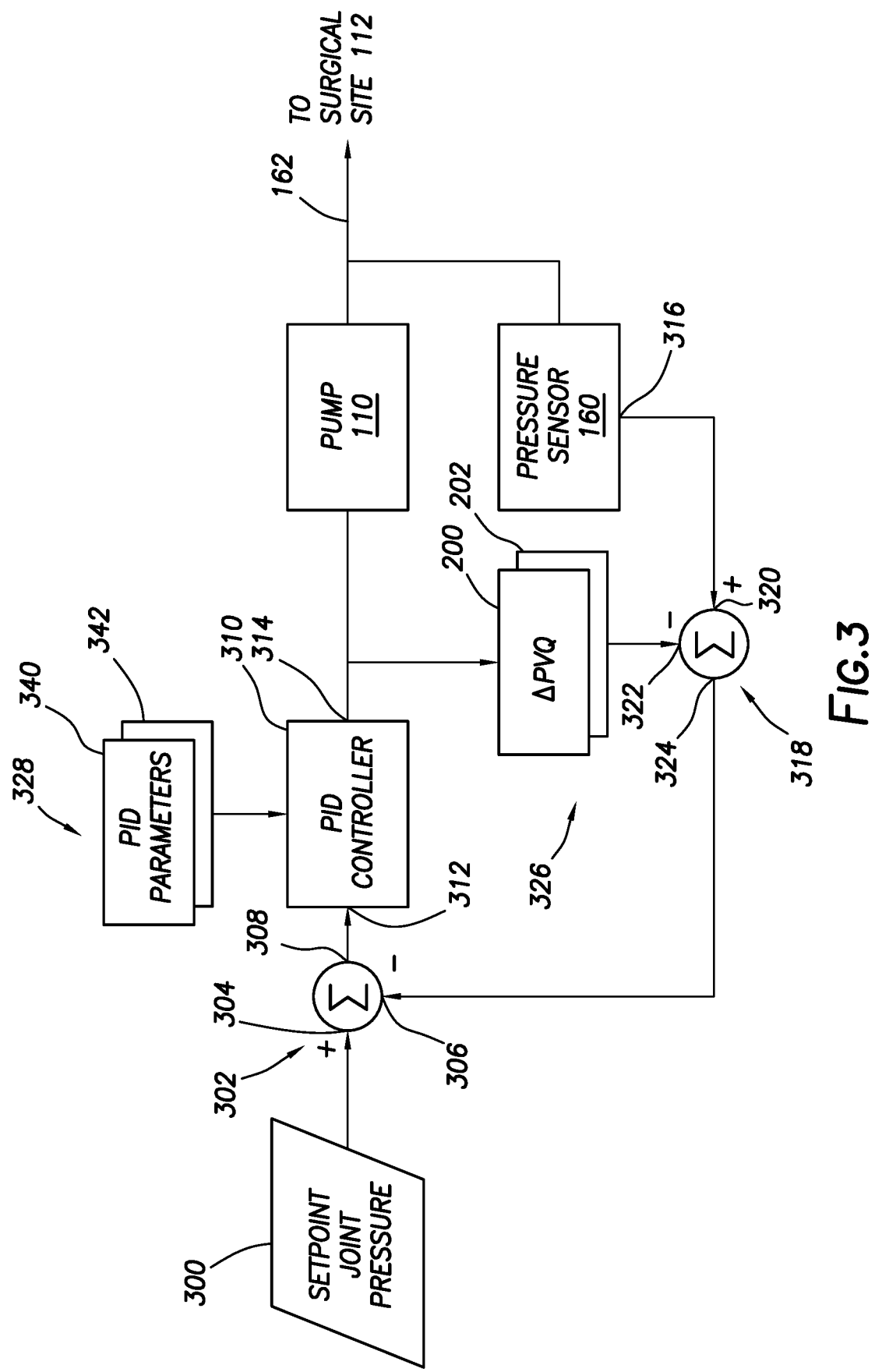
FIG. 3 shows a block diagram of a control loop in accordance with at least some embodiments.

FIG. 3 shows a block diagram of a control loop in accordance with at least some embodiments. FIG. 3 is largely hardware agnostic, as hardware implementation aspects of the example control loop will be discussed in greater detail below. In particular, FIG. 3 shows that a setpoint joint pressure 300 is provided by the surgeon (e.g., by way of user interface 150 (FIG. 1)). The setpoint joint pressure 300 is coupled to a summation or error block 302. That is, error block 302 defines an internal setpoint input 304, a feedback pressure input 306, and an error output 308. In the example embodiments of FIG. 3 the setpoint joint pressure 300 is provided directly to the internal setpoint input 304. PID controller 310 defines an error input 312 and a speed control output 314, and the error input 312 is coupled to the error output 308 of the error block 302. As the name implies, the PID controller 310 may implement a control philosophy whose output signal is based on a proportional component (i.e., proportional to the instantaneous value of the error signal on the error input 312), integral component (i.e., proportional to the value of the error signal over time), and a derivative component (i.e., based on the instantaneous rate of change of the value of the error signal). It is noted that referring to the component as a PID controller shall not be read to require all three components in every situation or mode. For example, in some cases the derivative component may not be present, or in some modes of operation the derivative component may be disabled, based on PID parameters (discussed more below).

In the example system, the PID controller 310 produces a signal on the speed control output 314 that is coupled to the peristaltic pump 110. More specifically, the peristaltic pump 110 comprises a motor (not specifically shown), and the signal on the speed control output 314 is coupled either directly to the motor or to a motor speed controller that controls speed of the motor (and thus the pump) based on the signal. The peristaltic pump 110 pumps surgical fluid to the surgical site by way of tube 162. The system further comprises pressure sensor 160 operationally coupled to the outlet of the pump 110, and thus is configured to measure pressure at the outlet of the pump prior to the balance of the tube 162. The pressure sensor 160 thus defines a pressure output 316.

The example control loop of FIG. 3 takes into account pressure drop across the length 164 (FIG. 1) of the tube 162 and inflow cannula 114 by way of the pressure feedback portion of the control loop. In particular, the example system includes a second error block 318 that defines a measured pressure input 320, a pressure drop input 322, and an inferred joint pressure output 324. The measured pressure input 320 is coupled to the pressure output 316 of the pressure sensor 160. The inferred joint pressure output 324 is coupled directly to the feedback pressure input 306 of error block 302, and the pressure drop input 322 is operatively coupled to one of a set of a delta-pressure versus flow (ΔPvQ) curves 326 (e.g., first curve 200, or second curve 202 of FIG. 2). The selected curve of the ΔPvQ curves 326 is operatively coupled to the speed control output 314 of the PID controller 310. Conceptually then, the system implements Equation (1) and creates an inferred joint pressure signal on the inferred joint pressure output 324 by subtracting a pressure drop (determined from the selected curve of the ΔPvQ curves 326 based on the signal on the speed control output 314) from the pressure signal applied to the measured pressure input 320. The inferred joint pressure signal created is applied to the feedback pressure input 306 of error block 302, and the error block 302 thus creates an error signal (on the error output 308) proportional to the difference between the setpoint joint pressure 300 and the inferred joint pressure signal on the inferred joint pressure output 324.

FIG. 3 further illustrates two sets of PID parameters 328, and in the example situation the PID parameters 328 comprise PID parameters 340 and PID parameters 342. Each group or set of PID parameters may take any suitable form and substance. For example, each set of PID parameters may include: a value or gain applied by the proportional component; a value or gain applied to the integral component; a value or gain applied to the derivative component; reset time of the integral component; loop time of the PID controller 310 (e.g., for microprocessor-based implementations, how often the various components are recalculated based on the signal on the error input 312); and initial values for the contributions of any PID components (e.g., initial integral values in spite of startup and thus no prior time integration).

An example implementation of the modes of operation can now be discussed in relation to the ΔPvQ curves 326 and PID parameters 328. In particular, FIG. 3 illustrates two ΔPvQ curves 326, and two sets of PID parameters 328, corresponding to an example two modes. Again, however, systems and related methods with two or more modes are contemplated. Example ΔPvQ curves 326 comprise a first curve 200 (also FIG. 2) or first relationship of fluid flow through the tube and pressure drop across the tube, and a second curve 202 (also FIG. 2) or second relationship of fluid flow through the tube and pressure drop across the tube. In a first mode, the example control loop uses the first curve 200 as part of determining or creating the inferred joint pressure signal applied to the feedback pressure input 306. In a second mode, the example control loop uses the second curve 202 as part of determining or creating the inferred joint pressure signal applied to the feedback pressure input. Switching between the example first mode and the second mode may take place based on commands received by way of the user interface 150 (FIG. 1), or may take place without specific user input (such as the fluid controller 108 (FIG. 1) receiving an indication that the shaver 120 or ablation device 132 have been activated).

Further in the first mode, the example control loop uses the PID parameters 340 in calculating the various contributions of the components of the PID controller 310 to create the signal on the speed control output 314. In the second mode, the example control loop uses the PID parameters 342 in calculating the various contributions of the components of the PID controller 310 to create the signal on the speed control output 314. It follows that PID parameters 340 and first curve 200 together are used in the example first mode, and PID parameters 342 and second curve 202 are used in the example second mode. As before, switching between the example first mode and the second mode may take place based on commands received by way of the user interface 150 (FIG. 1), or may take place without specific user input.

Assuming that first mode is the example aggressive mode, the PID parameters 340 thus implement a more aggressive control action. Likewise, assuming the second mode is the example conservative mode, the PID parameters 342 thus implement a less aggressive control action. For example, in the first mode the control system may, for an incremental drop in pressure measured by the pressure sensor, increase speed of the motor of the positive displacement pump a first amount; however, in the second mode the control system may, for an identical incremental drop in pressure measured by the pressure sensor, increase speed of the motor of the positive displacement pump a second amount less than the first amount. Similarly, in the first mode the control system may, for an incremental drop in pressure measured by the pressure sensor for a first length of time, increase speed of the motor of the positive displacement pump a third amount; however, in the second mode the control system may, for an identical incremental drop in pressure measured by the pressure sensor for the first length of time, increase speed of the positive displacement pump a fourth amount less than the third amount. These example reactions may be implemented in several forms. For example, proportional gain of the proportional component may be higher in the first mode than for the second mode. Likewise, integral gain may be higher in the first mode than for the second mode. In some cases, the first mode may have a non-zero derivative component contribution, while in the second mode there may be zero derivative contribution. Moreover, in addition to or in place of any of the previously discussed PID parameter differences, for microprocessor-based implementations the loop may be shorter in the first mode (e.g., 500 milliseconds) than in the in the second mode (e.g., 1 second), such that the control loop reacts differently in each mode.

FIG. 3 is presented to show one example control loop implementing example modes, where the control action of the PID controller 310 is responsive to a difference or error between the setpoint joint pressure and the feedback (inferred) joint pressure. However, the PID controller 310 is provided and operates on a difference signal, and thus utilizing the ΔPvQ curves 326 in the pressure feedback portion of the control loop is not required. Any change in the control parameters applied to the error block 302 (i.e., the internal setpoint input or the feedback pressure input) that results in the corresponding error signal applied to the PID controller 310 may be implemented. Thus, the specification turns to example control loops in accordance with other example embodiments where the relationship between fluid flow through the tube (and possibly inflow cannula) is implemented in relation to the signal provided to the internal setpoint input 304 of the error block 302, rather than in feedback pressure input 306.

Figure 4:
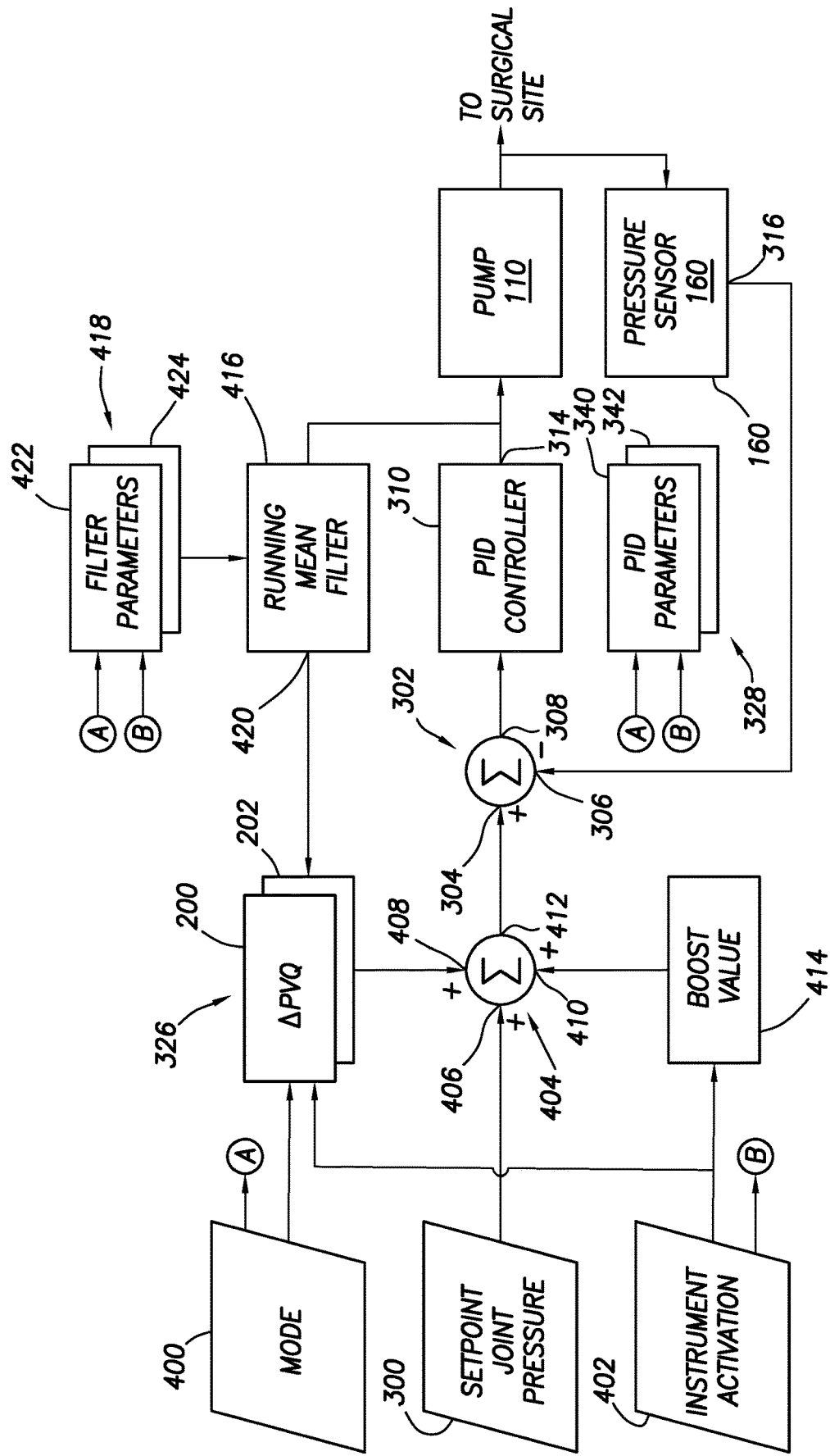
FIG. 4 shows a block diagram of a control loop in accordance with at least some embodiments.

FIG. 4 shows a block diagram of a control loop in accordance with at least some embodiments. As with FIG. 3, FIG. 4 is largely hardware agnostic, as hardware implementation aspects are discussed in great detail below. In particular, FIG. 4 shows that a setpoint joint pressure 300 and mode indication 400 are provided by the surgeon. Moreover, in some cases fluid controller 108 is provided an instrument activation indication 402 (such as from the shaver control system 128 and/or the ablation control system 138 (FIG. 1)). The setpoint joint pressure 300 is coupled to a summation block 404. Summation block 404 defines a setpoint input 406, a pressure drop input 408, an activation input 410, and a summation output 412. The summation output 412 is coupled to the internal setpoint input 304 of the error block 302, and as with FIG. 3 the error output 308 of error block 302 is coupled to PID controller 310.

The example mode indication 400 is operatively coupled such that the mode selects one of the ΔPvQ curves 326 (e.g., first curve 200, or second curve 202). Thus, based on a selected one of the ΔPvQ curves 326 and a signal (directly related to fluid flow through the peristaltic pump 110) on the speed control output 314 of the PID controller 310, a pressure drop signal is created and applied to the pressure drop input 408. Further, the instrument activation indication 402 is coupled to boost value block 414, and the boost value block 414 is operatively coupled to the activation input 410 of the summation block 404. When the instrument activation indication 402 becomes asserted, the boost value block 414 applies a non-zero value to the activation input 410, and when the instrument activation indication 402 is non-asserted, the boost value block 414 may apply a zero value to the activation input 410. In yet still other cases, the external device (e.g., the shaver control system 128 and/or ablation control system 138 (FIG. 1)) may provide a value indicative of fluid flow through respective instruments rather than a Boolean activation signal. In such cases the boost value block 414 may translate the signal from the external device to a boost value signal to be applied to the activation input 410.

As with the system of FIG. 3, in FIG. 4 the PID controller 310 produces a signal on the speed control output 314 that is directly or indirectly coupled to the pump 110. In the example system of FIG. 4, the speed control signal generated on the speed control output 314 is operatively coupled to the ΔPvQ curves 326 by way of a running mean filter 416. As the name implies, the running mean filter 416 filters the speed control signal generated on the speed control output 314 before use in conjunction with the selected curve of the ΔPvQ curves 326 to determine or calculate a pressure drop. The running mean filter 416 itself may have filter parameters 418 that change with the selected mode (as indicated by the bubble "A" connection to the mode indication 400). In the example aggressive mode, the averaging or filter time may be relatively short (e.g., 500 milliseconds, or one second). Such a relatively short filter time thus propagates more quickly speed control changes (and thus changes in flow provided by the pump) to the selected curve of the ΔPvQ curves 326. By contrast, in the example conservative mode the averaging or filter time may be relatively long (e.g., 2 seconds or more), making the pressure drop contribution applied to the pressure drop input 408 more slow to respond to the speed control changes (and thus changes in flow provided by the pump). The example PID parameters 328 operate similarly to FIG. 3, and the discussion is not repeated here so as not to unduly lengthen the specification. Finally, in the example control loop of FIG. 4 the pressure signal provided on the pressure output 316 of the pressure sensor 160 is tied directly to the feedback pressure input 306 of the error block 302.

The example control loop of FIG. 4 thus takes into account pressure drop across the length 164 (FIG. 1) of the tube 162 and inflow cannula 114 by way of the signal applied to the internal setpoint input 304. In particular, and for any particular mode, the example system determines or calculates a pressure drop signal using the selected curve of the ΔPvQ curves 326 and the running mean average speed signal (which is proportional to fluid flow) provided from the averaged output 420 of the running mean filter 416. The pressure drop is added to the setpoint joint pressure 300 at the summation block 404, and the summed value is provided as an internal setpoint input 304 to the error block 302. The error block 302 creates an error signal on the error output 308 based on the feedback pressure applied to the feedback pressure input 306, and the PID controller 310 acts accordingly on the error signal.

An example implementation of the modes of operation in FIG. 4 can now be discussed in relation to the ΔPvQ curves 326, PID parameters 328, and the filter parameters 418. In particular, FIG. 4 illustrates two ΔPvQ curves, two sets of PID parameters 328, two sets of filter parameters 418, corresponding to two example modes. Again, however, systems and related methods with two or more modes are contemplated. Example ΔPvQ curves 326 comprise a first curve 200 (also FIG. 2) or first relationship of fluid flow through the tube and pressure drop across the tube, and a second curve 202 (also FIG. 2) or second relationship of fluid flow through the tube and pressure drop across the tube. In a first mode, the example control loop uses the first curve 200 as part of creating the signal applied to the internal setpoint input 304. In a second mode, the example control loop uses the second curve 202 as part of creating the signal applied to the internal setpoint input 304. Switching between the example first mode and second mode may take place based on commands received by way of the user interface 150 (FIG. 1), or may take place without specific user input (such as the fluid controller 108 (FIG. 1) receiving the instrument activation indication 402).

Still referring to FIG. 4 and still considering the implementation of the modes of operation, FIG. 4 illustrates two sets of PID parameters 328 corresponding to the two example modes. The example PID parameters 328 comprise PID parameters 340 and PID parameters 342. Each group or set of PID parameters may take any suitable form and substance as discussed above in relation to FIG. 3. In the first mode, the example control loop uses the PID parameters 340 in calculating the various contributions of the components of the PID controller 310 to create the signal on the speed control output 314. In the second mode, the example control loop uses the PID parameters 342 in calculating the various contributions of the components of the PID controller 310 to create the signal on the speed control output 314. It follows that PID parameters 340 and first curve 200 together are used in the example first mode, and PID parameters 342 and second curve 202 are used in the example second mode. As before, switching between the example first mode and the second mode may take place based on commands received by way of the user interface 150 (FIG. 1), or may take place without specific user input (such as the fluid controller 108 (FIG. 1) receiving the instrument activation indication 402).

Still considering the implementation of the modes of operation, FIG. 4 illustrates two sets of filter parameters 418 corresponding to the two example modes. The example filter parameters 418 comprise filter parameters 422 and filter parameters 424. Each group or set of parameters may define how quickly the signal on the average output 420 reacts to changes in the speed signal. In the first mode, the running mean filter 416 uses the filter parameters 422 in filtering the speed signal to create the signal on the averaged output 420. In the second mode, the running mean filter 416 uses the filter parameters 424 in filtering the speed signal to create the signal on the averaged output 420. It follows that PID parameters 340, first curve 200, and filter parameters 422 are used in the example first mode, and PID parameters 342, second curve 202, and filter parameters 424 are used in the example second mode. As before, switching between the example first mode and the second mode may take place based on commands received by way of the user interface 150 (FIG. 1), or may take place without specific user input (such as the fluid controller 108 (FIG. 1) receiving the instrument activation indication 402).

Assuming, as before, that first mode is the example aggressive mode, the filter parameters 422 may implement shorter averaging times and thus faster response of the running mean filter 416 to changes in the speed control signal. Likewise, assuming the second mode is the example conservative mode, the filter parameters 424 may implement longer averaging times and thus slower response of the running mean filter 416 to changes in the speed control signal. The specification now turns to a discussion of actual joint pressure as it relates to example modes of operation.

Figure 5:
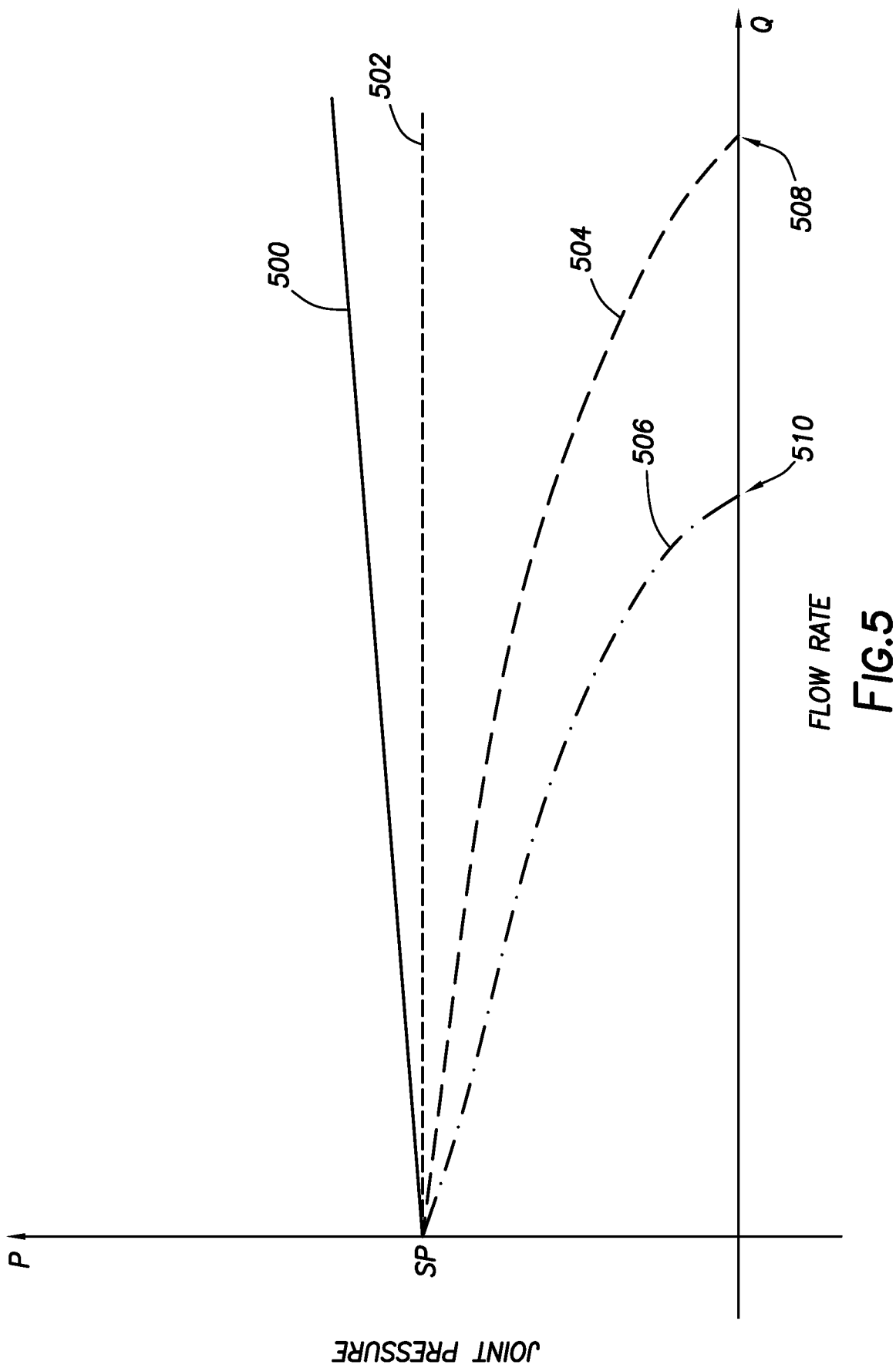
FIG. 5 shows a plot of joint pressure with respect to flow rate in example modes of operation, and in accordance with at least some embodiments.

FIG. 5 shows a plot of joint pressure with respect to flow rate in example modes of operation, and in accordance with at least some embodiments. In particular, the X axis (horizontal axis) is flow rate Q, and the Y axis (vertical axis) is joint pressure (P). The plot of FIG. 5 shows four relationships or curves: curve 500 (solid line); curve 502 (short-dashed line); curve 504 (long-dashed line); and curve 506 (dash-dot-dash line). In example systems and methods, the surgeon provides a setpoint joint pressure 300 (FIGS. 3 and 4), shown on the vertical axis of FIG. 5 as "SP." In an ideal system where pressure at the outlet of peristaltic pump 110 (FIG. 1) is known precisely, the precise relationship between pressure drop and fluid flow through tube 162 and inflow cannula 114 is known, and the compliance of the surgical site 112 is known, a fluid controller should be able to precisely control the actual joint pressure to match the setpoint pressure SP over the entire range of fluid flow, as shown by line or curve 502. However, in accordance with example embodiments, the fluid controller 108 (FIG. 1) is not provided the precise identity of the tube 162 and inflow cannula 114, and thus the precise relationship between pressure drop and fluid flow may not be known to the fluid controller 108. Moreover, in accordance with some example embodiments no calibration is performed regarding the relationship between pressure drop and fluid flow through the tube 162 and inflow cannula 114. In accordance with at least some embodiments the ΔPvQ curves (e.g., curves of FIG. 2) are created in advance and programmed in the fluid controller 108 prior to use (e.g., programmed during the manufacturing process).

Nevertheless, in accordance with example embodiments the ΔPvQ curves, and thus the various modes of operation, implement varying amounts of decreasing joint pressure (with constant setpoint pressure) with increasing flow through the joint. Curve 504 (long-dashed line) shows a first relationship of actual joint pressure to flow rate, where the pressure falls off to zero a particular flow rate 508. Likewise, curve 506 (dash-dot-dash line) shows a second relationship of actual joint pressure to flow rate, where the pressure falls off to zero a particular flow rate 510. Again, in most cases the actual joint pressure is not measured, and the control loop operates on an inferred joint pressure created directly or indirectly based on the selected curve of the ΔPvQ curves. The point is, in actual operation the fluid controller 108 (FIG. 1) may not actually maintain the surgical site 112 (FIG. 1) at the setpoint joint pressure 300 (FIG. 3). In some senses, the level of aggressiveness implemented by the fluid controller 108 may be correlated to how closely the selected mode controls actual joint pressure (in addition to the responsiveness of the control loop and related mechanisms). Thus, in an example first or aggressive mode, the fluid controller 108 may utilize a more aggressive relationship of pressure drop to fluid flow (e.g., curve 200 of FIG. 2), and in addition to the PID parameters and filter parameters utilized by the mode, the fluid controller 108 in the aggressive mode may achieve the relationship of actual joint pressure to flow rate shown by curve 504. Likewise, in an example second or conservative mode, the fluid controller 108 may utilize a less aggressive relationship of pressure drop to fluid flow (e.g., curve 202 of FIG. 2), and in addition to the PID parameters and filter parameters utilized by the mode, the fluid controller 108 in the conservative mode may achieve the relationship of actual joint pressure to flow rate shown by curve 506.

Some embodiments thus intentionally use ΔPvQ curves such that actual joint pressure decreases with increasing flow rate to lower the chances of extravasation. However, in yet still other cases the one or more of the ΔPvQ curves may be selected to more closely maintain actual joint pressure to setpoint joint pressure (e.g., curve 502). In yet still other cases, one or more of the ΔPvQ curves may be selected to drive actual joint pressure to above setpoint joint pressure with increasing flow rate (e.g., curve 500), representing an even more aggressive mode of operation. In some cases, all the possibilities illustrated by FIG. 5 may be implemented by a fluid controller as distinct modes of operation.

The various embodiments discussed to this point have assumed that the fluid controller 108 is neither provided an indication of the identity of the tube 162 and inflow cannula 114, nor involved in a calibration regarding the tube 162 and inflow cannula 114. Thus the actual relationship between flow rate and pressure drop across the tube 162 and inflow cannula 114 is not known. However, in yet still further cases the fluid controller 108 is provided an indication of the identity of the tube 162 and inflow cannula 114 and thus may know (e.g., based on information stored in the fluid controller 108) an actual relationship between flow rate and pressure drop across the tube 162 and inflow cannula 114. Alternatively but in the same vein, the fluid controller 108 may be involved in a calibration procedure such that an actual relationship between flow rate and pressure drop across the tube 162 and inflow cannula 114 is known. Nevertheless, in such example systems the modes of operation may be implemented. That is, even if the ΔPvQ curve is accurately known and fixed for all modes of operation selected, various modes may still be implemented by switching between different sets of PID parameters 328 (FIGS. 3 and 4), and switching between different filter parameters 418 (FIG. 4). The specification now turns to example hardware implementations.

Figure 6:
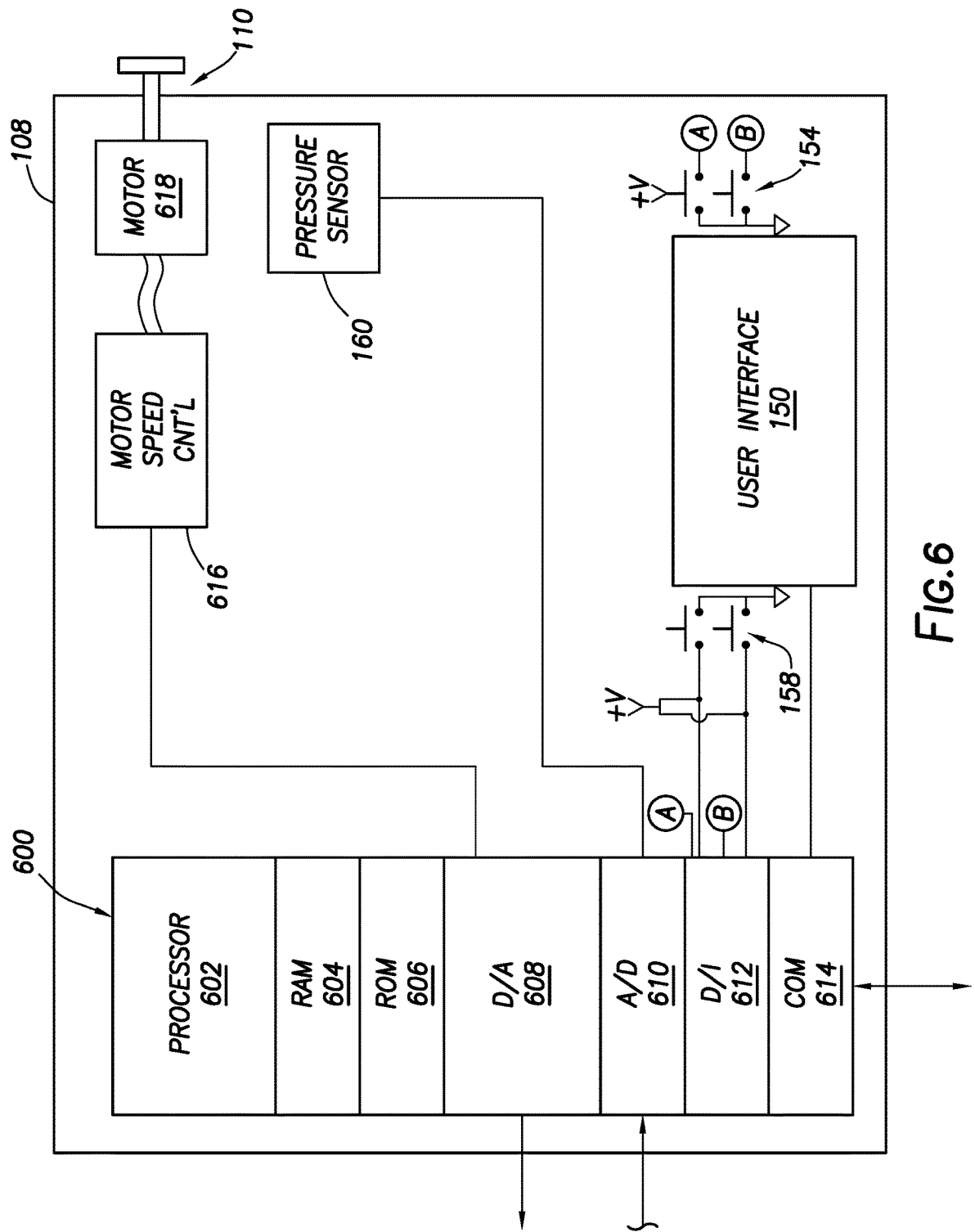
FIG. 6 shows, in block diagram form, an example fluid controller in accordance with at least some embodiments.

FIG. 6 shows, in block diagram form, an example fluid controller 108 in accordance with at least some embodiments. In particular, the example fluid controller 108 has a control system 600 coupled to various internal and external components. In the example system of FIG. 3, the control system 600 takes the example form of a microcontroller having processor 602 electrically coupled to random access memory (RAM) 604, read-only memory (ROM) 606, digital-to-analog (D/A) outputs 608, analog-to-digital (A/D) inputs 610, digital inputs (D/I) 612, as well as communication logic (COM) 614 sections. Though control system 600 is shown in the form of a microcontroller, in other cases individual components (i.e., an individual processor, RAM, ROM, etc.) may be combined to implement the functionality, or other devices such as FGPAs, ASICs, PLCs, and discrete components may be used. The example RAM 604 may be the working memory for the processor 602. ROM 606 may store programs and data in a non-volatile fashion, and the processor 602 may copy the programs and data from the ROM 606 to RAM 604 during execution of the programs. The digital-to-analog outputs 608 may be used to provide analog signals to other devices within the fluid management system, such as the motor speed controller 616 (discussed more below), or to external devices (e.g., a separate inflow pump controller, if used). The analog-to-digital inputs 610 may provide the control system 600 the ability to read analog signals, such as pressure measurements from the pressure sensor 160, or analog signals indicative of activation of various surgical instruments and their respective outflows (e.g., from the shaver control system 128 or the ablation control system 138). The digital inputs 612 may be used to receive information into the control system 600, such as digital signals indicative of activation of various surgical instruments (e.g., from the shaver control system 128 or the ablation control system 138), or information from example push buttons 154 and 158 (discussed more below). Finally, the communication logic 614 may be used for packet-based communications with internal or external devices (e.g., a system that has indications of activity of surgical instruments, user interface 150).

Regardless of the mechanism by which the fluid controller 108 receives various pieces of information, the control system 600 may implement the various modes of operation related to pumping surgical fluid to the surgical site by commanding peristaltic pump 110 to operate. As shown, the peristaltic pump 110 is turned by motor 618. The motor 618 may take any suitable form. For example, the motor 618 may be direct current (DC) electric motor, and thus the motor speed controller 616 provides a DC voltage to the electric motors which controls the speed of the output shaft. In other cases, the motor may be alternating current (AC) electric motor, and thus the motor speed controller 616 provides an AC voltage at varying voltage and frequency which controls the speed of the output shaft. In yet still other cases, the motor may be a pneumatic motor, and thus the motor speed controller 616 provides air at varying pressures, where the pressure controls the speed of the output shaft. Thus, regardless of the type of motor 618 implemented, the motor speed controller 616 controls the speed of the motor responsive to commands provided from the control system 600. While in the example system the command to the motor speed controller 616 is shown to be an analog signal, in other cases the motor speed controller 616 may receive commands in packet-based messages (e.g., through the communication logic 614). Finally, while the motor 618 is shown to directly couple to the peristaltic pump 110, in other cases various gears and/or belts may be used to transfer the rotational motion of the shaft of motor 618 to peristaltic pump 110. While FIG. 6 is based on having rotary peristaltic pumps, one having ordinary skill and with the benefit of this disclosure could modify the system to be used with other types of outflow pumps, such as linear peristaltic pumps or centrifugal pumps combined with flow measurement devices (as the flow rate through a centrifugal pumps may not be as directly related to speed as is a positive displacement pump (such as a peristaltic pump)).

Before proceeding, it is noted that the embodiments of FIG. 6 show the peristaltic pump 110 as an internal device to the fluid controller 108; however, in other cases the peristaltic pump 110 may be an external component to the fluid controller 108. Moreover, only one motor speed controller, motor, and pump are shown in FIG. 6, a fluid controller may implement two or more (e.g., an outflow peristaltic pump coupled to any of the various outflow instruments).

Thus, in example embodiments where the control system 600 is a processor 602, RAM 604, etc., as shown, the ROM 606 and RAM 604 (and possibly other non-transitory storage mediums) store instructions that implement the control loops of FIGS. 3 and 4 in the various modes. For example, the instructions, when executed by the processor, may cause the processor to: determine whether to operate in the first mode or the second mode; read the setpoint joint pressure from the user interface; read pressure measured by the pressure sensor; calculate a motor speed based on the setpoint joint pressure, the pressure measured by the pressure sensor, the first relationship of fluid flow through the positive displacement pump and the joint pressure, and the first set of control loop parameters; and calculate a motor speed based on the setpoint joint pressure, the pressure measured by the pressure sensor, the second relationship of fluid flow through the positive displacement pump and the joint pressure, and the second set of control loop parameters.

In yet still other cases, the control loop may be, in whole or in part, implemented in an ASIC or even in discrete components (e.g., capacitors, resistors, operational amplifiers), such that the discrete components operate to control the motor speed and thus the pump speed. In these situations, the modes of operation may be implemented by electrically controlled switches selecting switching in and out various circuit components (e.g., capacitors, resistors), or in other cases the fluid controller 108 may implement multiple discrete PID controllers hard wired with particular but different PID parameters, and thus changing modes may involve changing between the PID controllers themselves rather than just changing parameters of a single PID controller.

Figure 7:
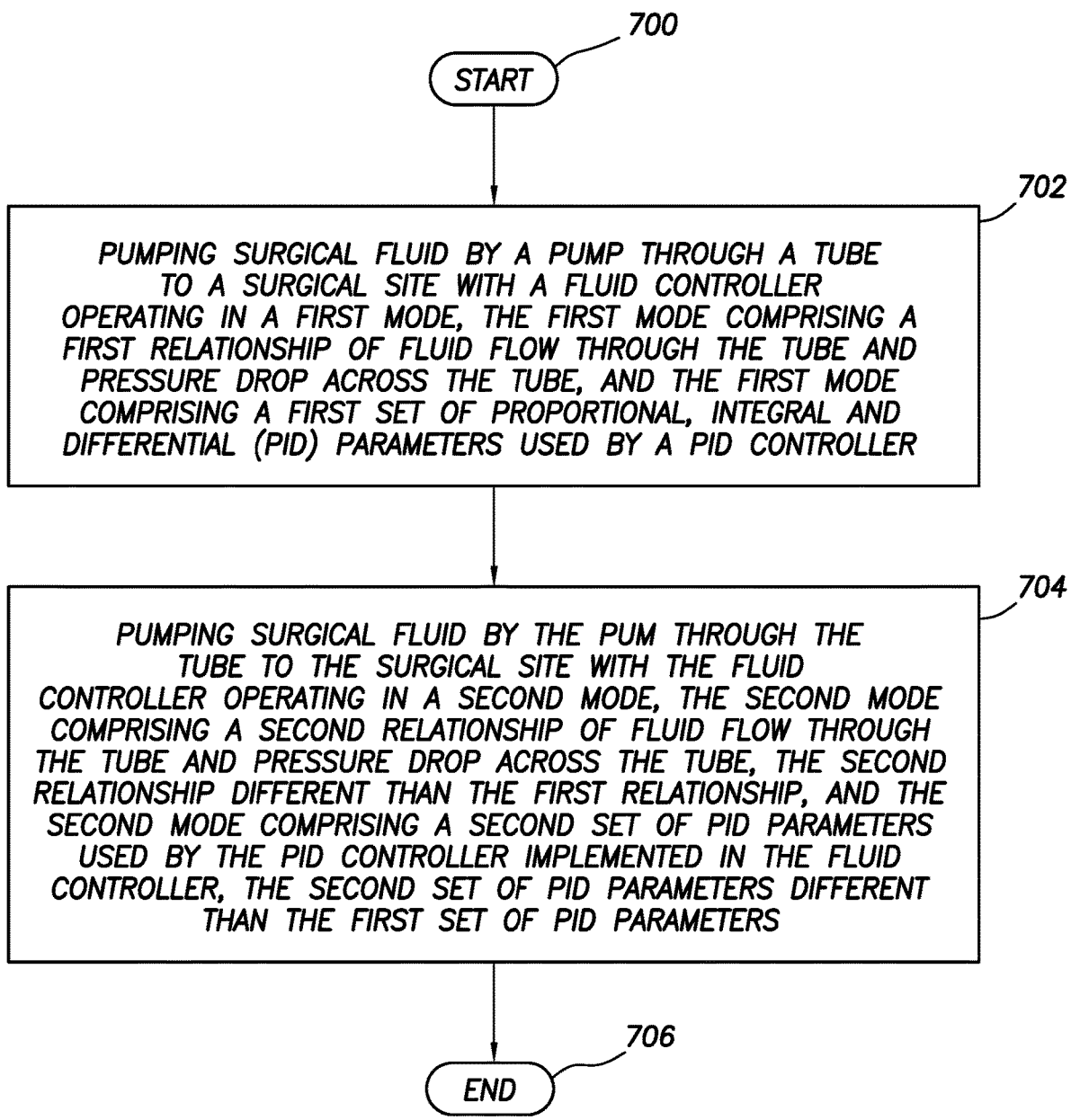
FIG. 7 shows a method in accordance with at least some embodiments.

FIG. 7 shows a method in accordance with at least some embodiments. In particular, the method starts (block 700) and comprises: pumping surgical fluid by a positive displacement pump through a tube to a surgical site with a fluid controller operating in a first mode, the first mode comprising a first relationship of fluid flow through the tube and pressure drop across the tube, and the first mode comprising a first set of proportional, integral, and differential (PID) parameters used by a PID controller (block 702); and then pumping surgical fluid by the positive displacement pump through the tube to the surgical site with the fluid controller operating in a second mode, the second mode comprising a second relationship of fluid flow through the tube and pressure drop across the tube, the second relationship different than the first relationship, and the second mode comprising a second set of PID parameters used by the PID controller implemented in the fluid controller, the second set of PID parameters different than the first set of PID parameters (block 704). Thereafter, the method may end (block 706), likely to be restarted.

The above discussion is meant to be illustrative of the principles and various embodiments of the present invention. Numerous variations and modifications will become apparent to those skilled in the art once the above disclosure is fully appreciated. For example, rather than pressure drop versus flow curves, the system may use curves that relate pump pressure to flow through the pump. Thus, in place of the running mean average filter the measured pressure could be applied to one or more curves that relate pump pressure to flow through the pump (the curve selected based on the mode), and the flow from the curve used as a basis for determining a pressure drop. It is intended that the following claims be interpreted to embrace all such variations and modifications.

What is claimed is:

1. A method comprising:
pumping surgical fluid by a pump through a tube and cannula to a surgical site by a fluid controller operating in a first mode, the first mode comprising a first relationship of fluid flow and pressure drop, and the first relationship of the first mode based on a first set of proportional, integral, and differential (PID) parameters used by a PID controller,
wherein pumping surgical fluid with the fluid controller in the first mode further comprises, for an incremental drop in joint pressure, increasing speed of the pump a first amount; and
pumping surgical fluid by the pump through the tube to the surgical site with the fluid controller operating in a second mode, the second mode comprising a second relationship of fluid flow and pressure drop, the second relationship different than the first relationship, and the second relationship of the second mode based on a second set of PID parameters used by the PID controller implemented in the fluid controller, the second set of PID parameters different than the first set of PID parameters,
wherein pumping surgical fluid with the fluid controller in the second mode further comprises, for the incremental drop in joint pressure, increasing speed of the pump a second amount that is different than the first amount.

2. The method of claim 1:
wherein pumping surgical fluid with the fluid controller in the first mode further comprises measuring outlet pressure at an outlet of the pump, determining a first value proportional to flow rate of the surgical fluid through the tube, and changing a control parameter based on the outlet pressure and the first value proportional to flow; and
wherein pumping surgical fluid with the fluid controller in the second mode further comprises measuring outlet pressure at the outlet of the pump, determining a second value proportional to flow rate of the surgical fluid through the tube, and changing the control parameter based on the outlet pressure and the second value proportional to flow.

3. The method of claim 2 wherein the control parameter is at least one selected from a group comprising: a feedback pressure supplied to a control loop; and an internal setpoint pressure supplied to the control loop.

4. The method of claim 1:
wherein pumping surgical fluid with the fluid controller in the first mode further comprises, for the incremental drop in joint pressure for a first length of time, increasing speed of the pump a third amount; and
wherein pumping surgical fluid with the fluid controller in the second mode further comprises, for the incremental drop in joint pressure for the first length of time, increase speed of the pump a fourth amount less than the third amount.

5. The method of claim 4 further comprises inferring joint pressure based on measuring pressure at an outlet of the pump.

6. The method of claim 1 further comprising:
receiving, by way of an input device associated with the fluid controller, a command to switch between the first mode and second mode; and
switching from the first mode to the second mode responsive to the command.

7. The method of claim 1 further comprising:
receiving, by the fluid controller, an indication that a surgical instrument within the surgical site has become operational; and
switching from the first mode to the second mode responsive to the indication.

8. The method of claim 7 wherein the surgical instrument is at least one selected from a group comprising: a shaver blade; a shaver burr; and an electro-surgical device.

9. The method of claim 8 wherein in the first relationship pressure drop increases with fluid flow at a first rate, and in the second relationship pressure drop increases with fluid flow at a second rate lower than the first rate.

10. The method of claim 8 wherein no calibration of pressure drop across the tube as a function of fluid flow is performed.

11. The method of claim 8 further comprising calibrating to determine the first relationship of fluid flow through and pressure drop across the tube and cannula.

12. A fluid controller for surgical procedures, the fluid controller comprising:
a user interface configured to accept a setpoint joint pressure;
a positive displacement pump that comprises a motor;
a pressure sensor configured to read pressure at an outlet of the positive displacement pump;
a control system coupled to the user interface, the pressure sensor, and the motor of the positive displacement pump, the control system configured to control speed of the motor by way of a feedback control loop, the feedback control loop operates based on control loop parameters, a pressure measured by the pressure sensor, and the setpoint joint pressure;
during a surgical procedure with a tube and a cannula, the control system is configured to operate in a first mode that utilizes a first relationship of fluid flow through the positive displacement pump and joint pressure, and the first mode utilizes a first set of control loop parameters,
wherein in the first mode the control system is configured to, for an incremental drop in pressure measured by the pressure sensor, increase speed of the motor of the positive displacement pump a first amount; and
during the surgical procedure with the tube and the cannula, the control system is configured to operate in a second mode that utilizes a second relationship of fluid flow through the positive displacement pump and joint pressure, the second mode different than the first mode, and the second mode utilizes a second set of control loop parameters, the second set of control parameters different than the first set of control parameters, wherein in the second mode the control system is configured to, for the incremental drop in pressure measured by the pressure sensor, increase speed of the motor of the positive displacement pump a second amount less than the first amount.

13. The fluid controller of claim 12:
wherein in the first mode the control system is configured to infer joint pressure based on the pressure measured by the pressure sensor, speed of the motor, and the first relationship to create a first inferred joint pressure, and configured to change a control parameter based on the first inferred joint pressure; and
wherein in the second mode the control system is configured to infer joint pressure based on the pressure measured by the pressure sensor, speed of the motor, and the second relationship to create a second inferred joint pressure, and configured to change a control parameter based on the second inferred joint pressure.

14. The fluid controller of claim 13 wherein the control parameter is at least one selected from a group comprising: a feedback pressure supplied to the feedback control loop; and an internal set point pressure supplied to the feedback control loop.

15. The fluid controller of claim 12 wherein the control system is further configured to switch between the first mode and second mode based on a command received by way of the user interface.

16. The fluid controller of claim 12 wherein the control system is further configured to receive an indication that a surgical instrument within a surgical site has become operational, and switch from the first mode to the second mode responsive to the indication.

17. The fluid controller of claim 16 wherein the indication is based on activation of at least one selected from a group comprising: a shaver blade; a shaver burr; and an electrosurgical device.

18. The fluid controller of claim 12 wherein the control system further comprises:
a processor; and
a memory coupled to the processor, the memory stores instructions that, when executed by the processor, cause the processor to:
determine whether to operate in the first mode or the second mode;
read the setpoint joint pressure from the user interface;
read pressure measured by the pressure sensor;
calculate a motor speed based on the setpoint joint pressure, the pressure measured by the pressure sensor, the first relationship of fluid flow through the positive displacement pump and the joint pressure, and the first set of control loop parameters; and
calculate a motor speed based on the setpoint joint pressure, the pressure measured by the pressure sensor, the second relationship of fluid flow through the positive displacement pump and the joint pressure, and the second set of control loop parameters.

19. The fluid controller of claim 12 wherein the positive displacement pump is a peristaltic pump.

20. A fluid controller for surgical procedures, the fluid controller comprising:
a user interface configured to accept a setpoint joint pressure;
a positive displacement pump that comprises a motor;
a pressure sensor configured to read pressure at an outlet of the positive displacement pump;
a control system coupled to the user interface, the pressure sensor, and the motor of the positive displacement pump, the control system configured to control speed of the motor by way of a feedback control loop, the feedback control loop operates based on control loop parameters, a pressure measured by the pressure sensor, and the setpoint joint pressure;
the control system is configured to operate in a first mode that utilizes a first relationship of fluid flow through the positive displacement pump and joint pressure, and the first mode utilizes a first set of control loop parameters; and
the control system is configured to operate in a second mode that utilizes a second relationship of fluid flow through the positive displacement pump and joint pressure, the second mode different than the first mode, and the second mode utilizes a second set of control loop parameters, the second set of parameters different than the first set of parameters;
wherein in the first mode the control system is configured to, for an incremental drop in pressure measured by the pressure sensor, increase speed of the motor of the positive displacement pump a first amount;
wherein in the second mode the control system is configured to, for the incremental drop in pressure measured by the pressure sensor, increase speed of the motor of the positive displacement pump a second amount less than the first amount;
wherein in the first mode the control system is configured to, for an incremental drop in pressure measured by the pressure sensor for a first length of time, increase speed of the motor of the positive displacement pump a third amount; and
wherein in the second mode the control system is configured to, for an incremental drop in pressure measured by the pressure sensor for a first length of time, increase speed of the positive displacement pump a fourth amount less than the third amount.

* * * * *